US00PP36228P2

(12) United States Plant Patent
Robacker et al.

(10) Patent No.: US PP36,228 P2
(45) Date of Patent: Oct. 29, 2024

(54) ***VITEX* PLANT NAMED 'V12-2-1'**

(50) Latin Name: *Vitex agnus-castus*
Varietal Denomination: V12-2-1

(71) Applicant: University of Georgia Research Foundation, Inc., Athens, GA (US)

(72) Inventors: Carol Robacker, Peachtree City, GA (US); Sherrod Baden, Milner, GA (US); Allen Byous, Thomaston, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 18/445,801

(22) Filed: Feb. 8, 2024

(51) Int. Cl.
*A01H 5/00* (2018.01)
*A01H 6/50* (2018.01)

(52) U.S. Cl.
USPC ..... Plt./226

(58) Field of Classification Search
USPC ..... Plt./226
See application file for complete search history.

(56) References Cited

U.S. PATENT DOCUMENTS

PP27,376 P3 * 11/2016 Robacker ..... Plt./226

* cited by examiner

*Primary Examiner* — Karen M Redden
(74) *Attorney, Agent, or Firm* — Thomas | Horstemeyer, LLP

(57) ABSTRACT

A new and distinct cultivar of the *Vitex agnus-castus* plant named 'V12-2-1' is characterized by a combination of its heavy blooming with violet-blue flowers, its compact form, its short panicle length with closely spaced subpanicles and whoris of florets, and its tendency to re-bloom in late summer or fall.

7 Drawing Sheets

Genus and species *Vitex agnus-castus*.

Varietal denomination: The new *Vitex agnus-castus* claimed is of the cultivar denominated 'V12-2-1'.

BACKGROUND OF THE INVENTION

The present invention relates to a new and distinct cultivar of the ornamental flowering shrub/small tree *Vitex agnus-castus* hereinafter referred to by the varietal domination 'V12-2-1'. The new *Vitex* 'V12-2-1' is a product of a breeding program conducted by the inventors in Athens and Griffin, GA. An objective of the *Vitex* breeding program is to produce a tough and adaptable drought-tolerant plant cultivar with commercial value. This cultivar 'V12-2-1' has significant commercial and home gardener appeal with heavy blooming of violet-blue flowers, small and compact form, thick dense panicles, and tendency to rebloom late summer and fall. These and other qualities are enumerated herein.

Pedigree and history: 'V12-2-1' originated from a cross in 2005 at the University of Georgia Horticulture Farm in Watkinsville, GA. The cultivars 'Shoal Creek' and 'Silver Spires' were placed in a cage with bees to facilitate cross pollination. Seeds were collected from 'Shoal Creek'. These seeds may have resulted from self or cross pollination. They were sown in a greenhouse in Watkinsville and selections were made among the seedlings in 2006. One of the selections, labeled V0504B-38, was asexually propagated by softwood cuttings. Three replicates were planted in a field plot in Griffin, GA (cold hardiness zone 8a) in June 2009. Seeds from open-pollination of V0504B-38 were collected in November 2011 and were sown in a greenhouse in Griffin, GA during March 2012. One plant was selected based on container performance and planted into the field in Griffin, GA in 2013. This plant was labeled V12-2-1. Softwood cuttings were made from this selection in 2015. In 2016, three replicates were planted in a completely randomized design in a field plot in Griffin, GA, and two replicates were planted in Blairsville, GA (cold hardiness zone 7a) in July 2017. These plants were evaluated throughout the growing season for growth habit, floral and foliate characteristics, plant form and height, cold hardiness, date of first bloom, and disease or insect damage.

The original 'V12-2-1' plant has been evaluated in Griffin, GA for 9 years and the clonally propagated plants have been evaluated in Griffin, GA for 6 years and in Blairsville, GA for 5 years. In Griffin, GA, heights and widths were measured in November of each year. Winter cold and spring frost damage were assessed each spring in Griffin and Blairsville, GA.

Flower panicles were measured each year in June and number of panicles per compound panicle were counted. Date of first bloom was recorded each year, and plants were rated for reblooming at the end of July, August, September, and October of each year. Observation for disease or insect damage was continuous throughout the summer.

Height after six seasons in the field is 179 cm. Width is 264 cm after six seasons in the field. Stems are R.H.S. (Royal Horticultural Society, 2007) N199A grey-brown with a diameter of 4-5 mm.

The trunk color is N199A grey-brown with 156A grey-white areas. Stem striations begin on large stems or trunks at about 5 cm, with a diameter of 2.5-5 cm. Smaller stems are mostly smooth and larger stems start to crack by 5 cm. Leaves emerge with green 137C upper surface, changing to a deeper green 137A during the summer, and becoming green N137B in the fall. Lower leaf surface is greyed-green 191A during the summer and 191B in fall.

Leaves are palmately-compound, 9 cm×10 cm, with five-seven leaflets. Margins are mostly entire, with acute apices and bases. The upper leaf surface has very sparse, short hairs with somewhat glandular surface, while the lower surface has more hairs, especially along midvein, with a very glandular surface. Leaves are slightly waxy above, dull underneath. Venation is simple. Leaf arrangement on stems is opposite to slightly alternate.

Flower buds are violet-blue 95D. Flowers occur in an elongated compound panicle, with longest subpanicle 9×2.8 cm. Flowers are 95C violet-blue at peak of bloom on the upper surface, and 93D violet-blue edged with 93B violet-blue on the lower surface. The peduncle is grayed-green 194A. The number of individual flowers per inflorescence ranges from 400-500+. Sepals are grayed-green 193A.

SUMMARY OF THE INVENTION

The new *Vitex* cultivar 'V12-2-1' has not been observed under all possible environmental conditions. The phenotype may vary somewhat with variations in environment and cultural practices such as temperature, water and fertility levels, soil types, and light intensity without, however, any variance in genotype. The *Vitex* genus consists of about 250 species of shrubs and trees. About 18 species are cultivated, and most of these are grown as ornamentals. *Vitex agnus-castus* is a shrub that can be pruned to be a small tree with single or multiple trunks. It is usually winter hardy in USDA zones 6 to 9 but can be grown in colder climates where it dies back to the ground in the winter and re-grows and flowers as a shrub in the spring and summer. Once established, this plant has good drought tolerance, and is very attractive to bees and other pollinators. The new plant is expected to be distributed for landscape use in the U.S. and perhaps in other countries.

'V12-2-1' plants have been evaluated for nine years at the Griffin, GA site. Height and width data were collected and week of first bloom was recorded each year on the plants in Griffin. Winter cold and spring frost damage was assessed each spring. Length of the main axis and width of the entire compound panicle was measured each June. Repeat bloom was scored at the end of July, August, September, and October.

The following characteristics have been consistently observed, and, to the best knowledge of the inventor, their combination forms the unique characteristics of 'V12-2-1' as a new and distinct cultivar. In combination, these traits set 'V12-2-1' apart from all other existing varieties of *Vitex* known to the inventors:

1. Heavy blooming with violet-blue flowers in showy compound panicles (FIGS. 1, 2);
2. Compact Form (FIG. 1, Tables 1, 2);
3. Blooms one week later than parent cultivars (Table 3);
4. Short panicle length, with closely spaced subpanicles and whorls of florets creating dense appearance (FIG. 2, Table 4);
5. Tendency to re-bloom later in summer or fall (Table 5).

COMPARISON WITH OTHER VARIETIES

The new variety of *Vitex* 'V12-2-1' can be compared to the cultivars from which it was derived, 'Shoal Creek' and 'Silver Spires' and a widely grown blue-flowered cultivar 'Abbeville Blue' (unpatented). 'V12-2-1' plants have been evaluated in field plots in Griffin, GA and in Blairsville, GA. One plant each of 'Shoal Creek', 'Silver Spires', and 'Abbeville Blue' were planted in a Griffin, GA field plot in 2010, and one plant of 'V12-2-1' was planted in 2013. In 2016, three vegetatively propagated one-year old liners of 'V12-2-1' and one-year old liners of 'Shoal Creek' and 'Abbeville Blue' were planted in a Griffin, GA field plot in a randomized design along with several other genotypes.

Flowers of 'V12-2-1' are violet-blue 95C, similar to the color of 'Shoal Creek' and 'Abbeville Blue'. In a field planting established in 2016, height and width measured after six growing seasons indicated that 'V12-2-1' is significantly shorter and narrower than 'Shoal Creek' and 'Abbeville Blue' (Table 1). The mean height of three 'V12-2-1' plants was 179 cm compared to 400 cm for 'Shoal Creek' and 393 cm for 'Abbeville Blue'. The width of 'V12-2-1' was 264 cm compared to 480 cm for 'Shoal creek' and 518 cm for 'Abbeville Blue'. Similarly, measurements of plants planted in different years but with the same number of years in the field, showed that 'V12-2-1' is much smaller than 'Shoal Creek', 'Abbeville Blue' and 'Silver Spires' (Table 2). After 7 years growth, 'V12-2-1' was only 197 cm tall, compared to 'Shoal Creek' at 428 cm, 'Abbeville Blue' at 386 cm and 'Silver Spires' at 348 cm.

Cultivar 'V12-2-1' blooms about one to two weeks later than 'Shoal Creek' and 'Abbeville Blue' and is similar in bloom time to 'Silver Spires' (Table 3). The first week of flowering for 'V12-2-1' in Griffin is early to mid-June. 'Shoal Creek' and 'Abbeville Blue' bloom end of May to early June.

The panicles of 'V12-2-1' appear more dense or thicker than typical panicles of *Vitex* due to having an average of more than 4 subpanicles on a relatively short panicle and a short distance between the whorls of florets (FIG. 2, Table 4). The compound panicles of 'V12-2-1' are an average of 121 mm long, significantly shorter than the parent cultivars 'Shoal Creek' with a length of 254 mm and 'Silver Spires' with a length of 177 mm. Similarly, the standard cultivar 'Abbeville Blue' has panicles of 224 mm in length (Table 4). Compound panicle width of 'V12-2-1' is also narrower than 'Shoal Creek' and 'Abbeville Blue', but similar to 'Silver Spires'. Panicle width of 'V12-2-1' is 37 mm versus 'Shoal Creek' at 59 mm and 'Abbeville Blue' at 49 mm. The mean number of subpanicles of 'V12-2-1' is 4.7, similar to 'Abbeville Blue' and 'Silver Spires'. 'Shoal Creek' has only an average of 3.1 subpanicles, significantly fewer than the other cultivars (Table 4). The distance between the whorls of florets on the panicles on 'V12-2-1' is a mean of 14.6 mm, which is shorter than both 'Shoal Creek' and 'Abbeville Blue', with lengths of about 25 mm and 23 mm respectively. Therefore, the florets on 'V12-2-1' are more closely spaced (FIG. 2, Table 4).

Repeat bloom is a desired quality for landscape plants. The plants were evaluated near the end of the months of July, August, September, and October for amount of flowering as compared to peak bloom that occurs in June. Ratings from 0 to 4 were assigned, where 0 was no repeat bloom, up to 4, where flowering was at least 60% full bloom. Repeat bloom was averaged over four 'V12-2-1' plants in the Griffin field plot and compared to the check cultivars (Table 5). 'V12-2-1' had a higher repeat bloom than 'Shoal Creek', 'Abbeville Blue' and 'Silver Spires'. Repeat bloom was highest in July and October, though some flowering occurred in August and September as well.

The new *Vitex* 'V12-2-1' is readily propagated through cuttings. Cuttings rooted at a rate of over 70%. After 2 months, cuttings can be transferred to one-gallon containers using a well-drained potting mix. From cutting to saleable plant is about 8 months. No insect or disease problems have been noted in potted plants maintained outside the greenhouse, or in field plants. After landscape establishment, plants may be pruned to one or more trunks to form into a tree or may be unpruned to form into a shrub. Once established, the plants are very drought resistant.

The new variety 'V12-2-1' is a small *Vitex* with rounded form that blooms heavily in early summer with violet blue flowers and tends to repeat bloom in late summer and early fall.

'V12-2-1' is propagated vegetatively by stem cuttings.

TABLE 1

Height and width (cm) of 'V12-2-1', 'Shoal Creek' and 'Abbeville Blue' in a field plot in Griffin, GA that was established in June 2016 from one-year old liners. Data was collected in November 2021 from plants in the field for six growing seasons.

| Genotype | Rep # | Height (cm) | Width (cm) |
|---|---|---|---|
| 'V12-2-1' | 3 | 179 ± 10.8* | 264 ± 24.7* |
| 'Shoal Creek' | 1 | 400 | 480 |
| 'Abbeville Blue' | 1 | 393 | 518 |

*Standard error of the means at the 95% confidence level

TABLE 2

Height (cm) of 'V12-2-1', 'Shoal Creek', 'Abbeville Blue' and 'Silver Spires' in a field plot in Griffin, GA. Plants were planted in various years. Data was collected November each year, and calculations were based on number of years in the field.

| Genotype | Rep # | Height at 6 yrs (cm) | Rep # | Height at 7 years (cm) |
|---|---|---|---|---|
| 'V12-2-1' | 4 | 193 ± 15.5* | 4 | 197 ± 14.4* |
| 'Shoal Creek' | 2 | 378 ± 22 | 1 | 428 |
| 'Abbeville Blue' | 3 | 364 ± 21 | 2 | 386 ± 39 |
| 'Silver Spires' | 2 | 312 ± 25.5 | 2 | 348 ± 8.5 |

*Standard error of the means at the 95% confidence level

TABLE 3

Week of first bloom for 'V12-2-1', 'Shoal Creek', 'Abbeville Blue', and 'Silver Spires' in a Griffin field plot in 2016, 2018, 2020 and 2022. The number in parentheses is the number of plants that bloomed on that date.

| Genotype | 2016 | 2018 | 2020 | 2022 |
|---|---|---|---|---|
| 'V12-2-1' | 6-6 (1) | 6-11 (1)<br>6-18 (3) | 6-8 (3)<br>6-15 (1) | 6-6 (3)<br>6-13 (1) |
| 'Shoal Creek' | 5-30 (1) | 6-4 (2) | 6-1 (2) | 5-30 (2) |
| 'Abbeville Blue' | 5-30 (2) | 6-4 (2) | 6-1 (3) | 5-30 (2)<br>6-6 (1) |
| 'Silver Spires' | 6-6 (2) | 6-4 (1)<br>6-11 (1) | 6-15 (2) | 6-6 (2) |

TABLE 4

Comparison of morphological traits of compound panicles of 'V12-2-1', 'Shoal Creek', 'Abbeville Blue', and 'Silver Spires'. Panicles were collected from field-grown plants in full sun in Griffin, Georgia in June 2020.

| Cultivar | Panicle Length[1] (mm) | Compound panicle width[2] (mm) | Number of subpanicles per panicle | Distance between whorls of florets[3] (mm) |
|---|---|---|---|---|
| 'V12-2-1' | 121a[4] | 37.1a | 4.7bc | 14.6a |
| 'Shoal Creek' | 254d | 58.7c | 3.1a | 25.2b |
| 'Abbeville Blue' | 224c | 49.1b | 4.8c | 23.0b |
| 'Silver Spires' | 177b | 34.0a | 4.2ab | 17.0a |

[1]Length of the main axis of the panicle,
[2]width of the compound panicle (includes the subpanicles), number of subpanicles, and
[3]distance between the second and third whorls of florets from the base of the main axis. Data given is the mean measured on nine typical compound panicles on plants of a similar age.
[4]Means of lengths, widths, subpanicle numbers and distance between whorls of florets were compared across genotypes using t-tests. Means followed by different letters are significantly different at $P < 0.01$.

TABLE 5

Repeat flowering in 2020 and 2021 as rated monthly on 'V12-2-1', 'Shoal Creek', 'Abbeville Blue' and 'Silver Spires' in a field plot in Griffin, Ga.

| | 2020 | | | |
|---|---|---|---|---|
| Cultivar | July 28 | August 27 | September 30 | October 30 |
| 'V12-2-1' | 1.75* | 0.75 | 1.0 | 1.75 |
| 'Shoal Creek' | 0 | 0.5 | 1.0 | 0 |
| 'Abbeville Blue' | 0 | 0.33 | 1.3 | 0 |
| 'Silver Spires' | 0 | 0 | 0 | 0 |
| | 2021 | | | |
| Cultivar | July 29 | August 30 | September 27 | October 26 |
| 'V12-2-1' | 2.75 | 1 | 0.5 | 0.75 |
| 'Shoal Creek' | 0 | 0 | 0.5 | 0.5 |
| 'Abbeville Blue' | 0 | 0 | 0.3 | 0.3 |
| 'Silver Spires' | 1.0 | 0 | 0 | 0 |

*Repeat flowering was rated using the following scale: 0 = no flowering; 1 = 10% full bloom; 2 = 20 to 30% full bloom; 3 = 40 to 50% full bloom; 4 = at least 60% full bloom.

BRIEF DESCRIPTION OF THE FIGURES

The accompanying colored photographic illustrations show the overall appearance and distinct characteristics of the new cultivar of *Vitex agnus-castus* 'V12-2-1' showing the colors as true as possible. Colors in the photographs may differ slightly than the color values cited in the detailed botanical description, which accurately describes the colors of the new *Vitex* 'V12-2-1'. The photographs were taken of plants grown outdoors in Griffin, GA on Jun. 23, 2020.

FIG. 1 is a photograph depicting the overall plant habit and size of 'V12-2-1' as compared to 'Shoal Creek' and 'Abbeville Blue'. 'V12-2-1' is smaller and has a more rounded form than the comparison cultivars.

FIG. 2 is a close-up view of the panicles of 'Shoal Creek', 'Abbeville Blue', 'Silver Spires', and 'V12-2-1'. The panicles of 'V12-2-1' are shorter and more dense than those of the comparison cultivars.

DETAILED BOTANICAL DESCRIPTION

Figure 1A:
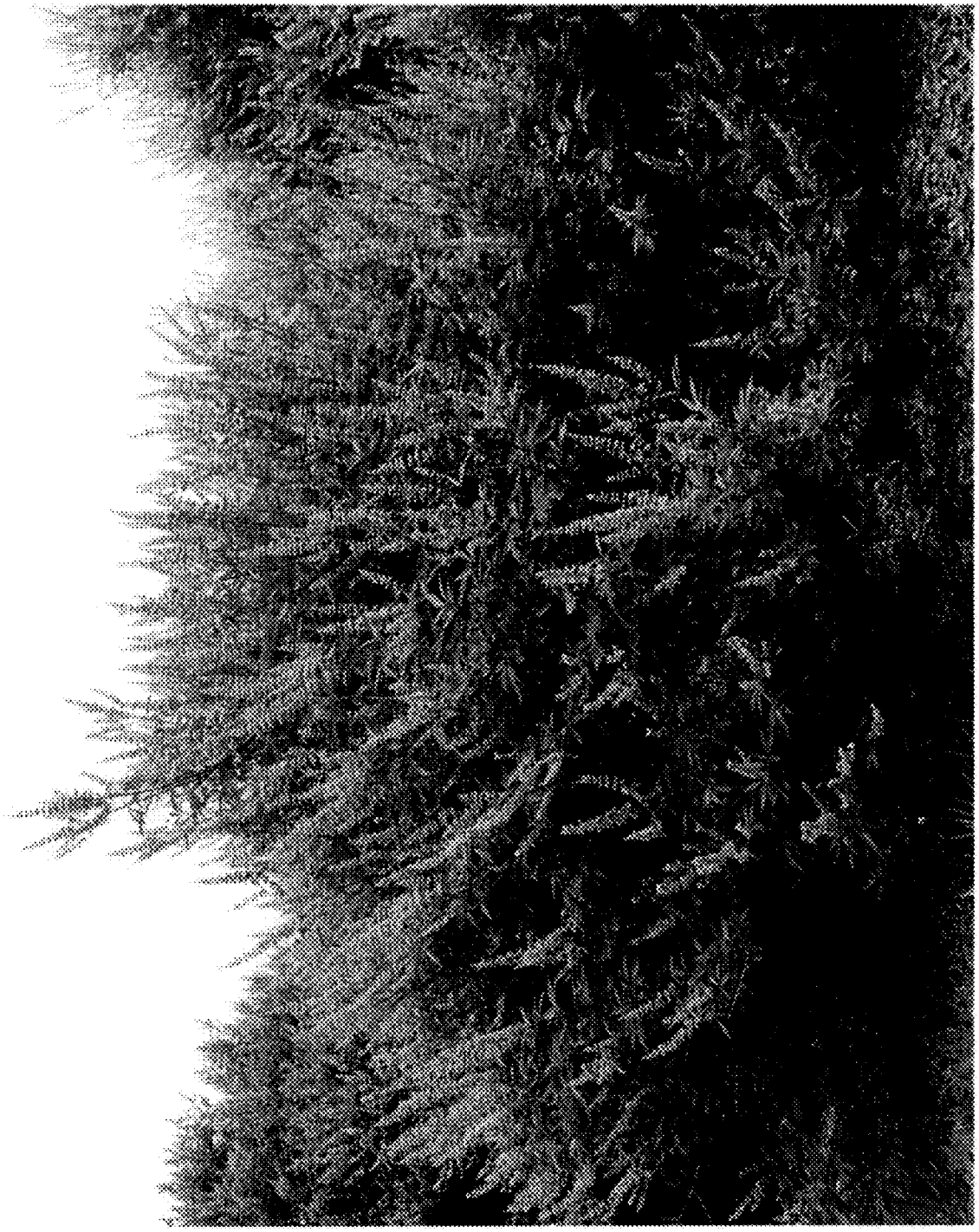
FIG. 1A shows 'Shoal Creek'.
Figure 1B:
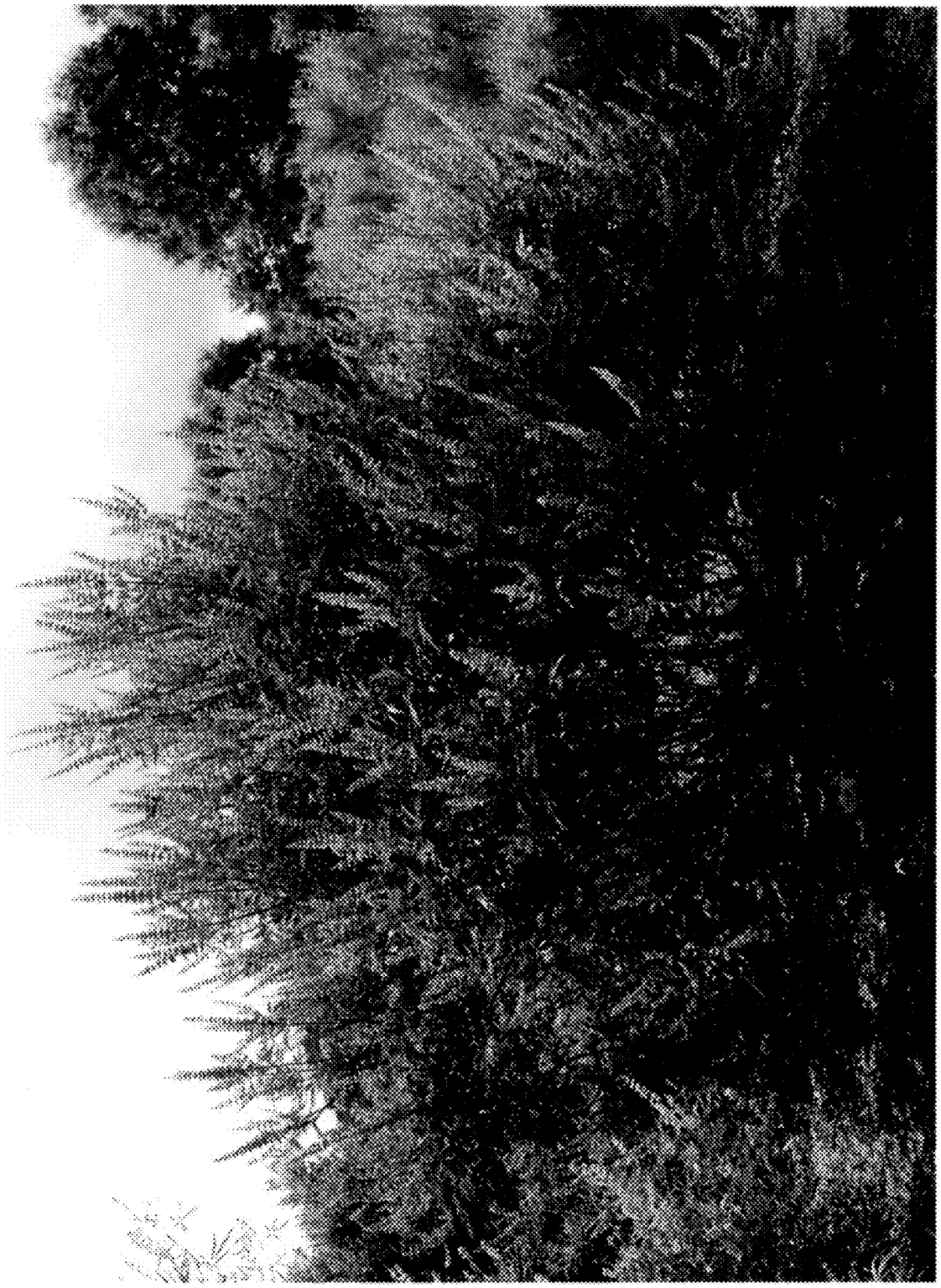
FIG. 1B shows 'Abbeville Blue'.
Figure 1C:
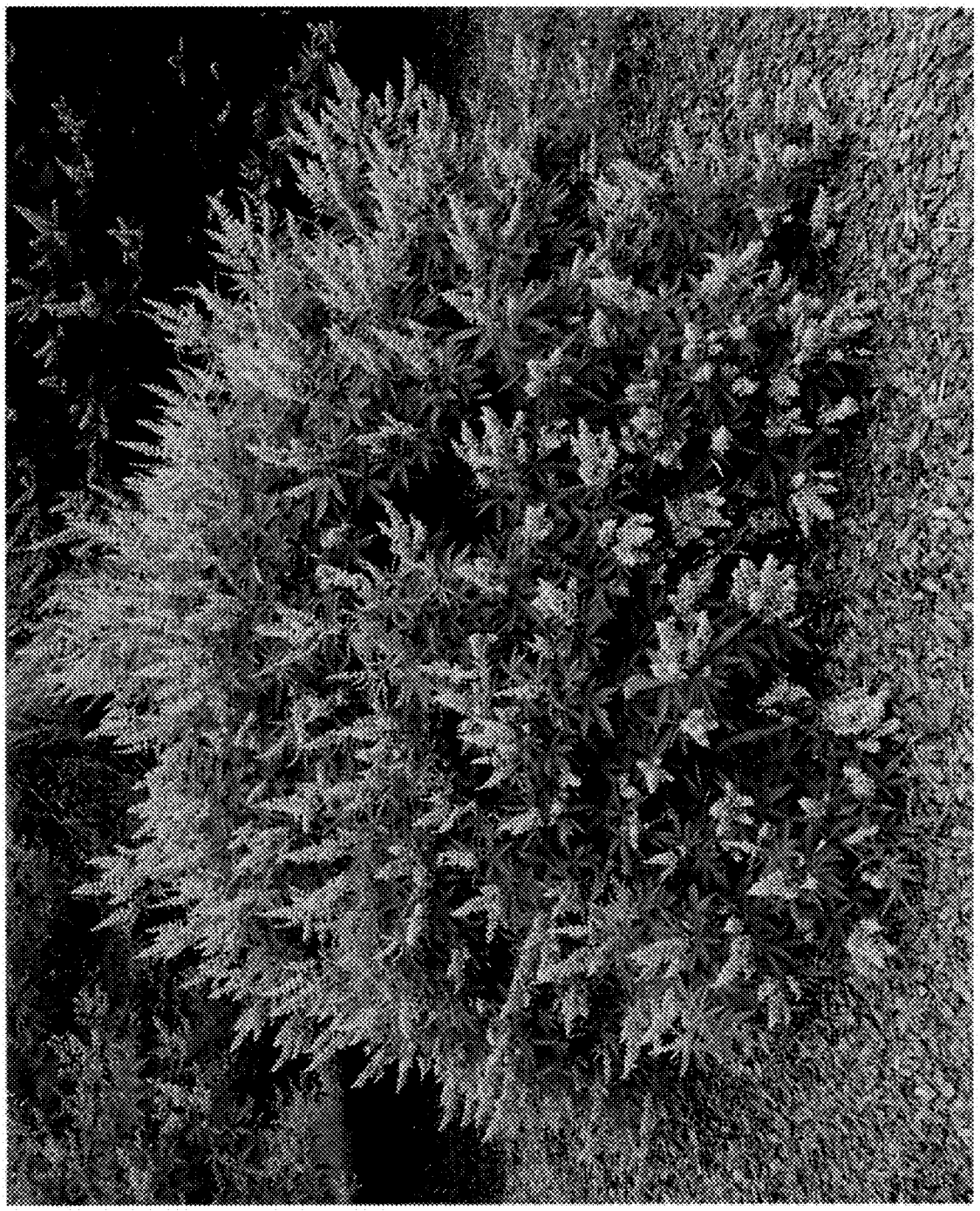
FIG. 1C shows 'V12-2-1'. These plants were planted in a field plot in Griffin, Ga in June 2016. Photos were taken on Jun. 23, 2020, in Griffin, Ga. 'V12-2-1' is smaller and has a more rounded form.
Figure 2A:
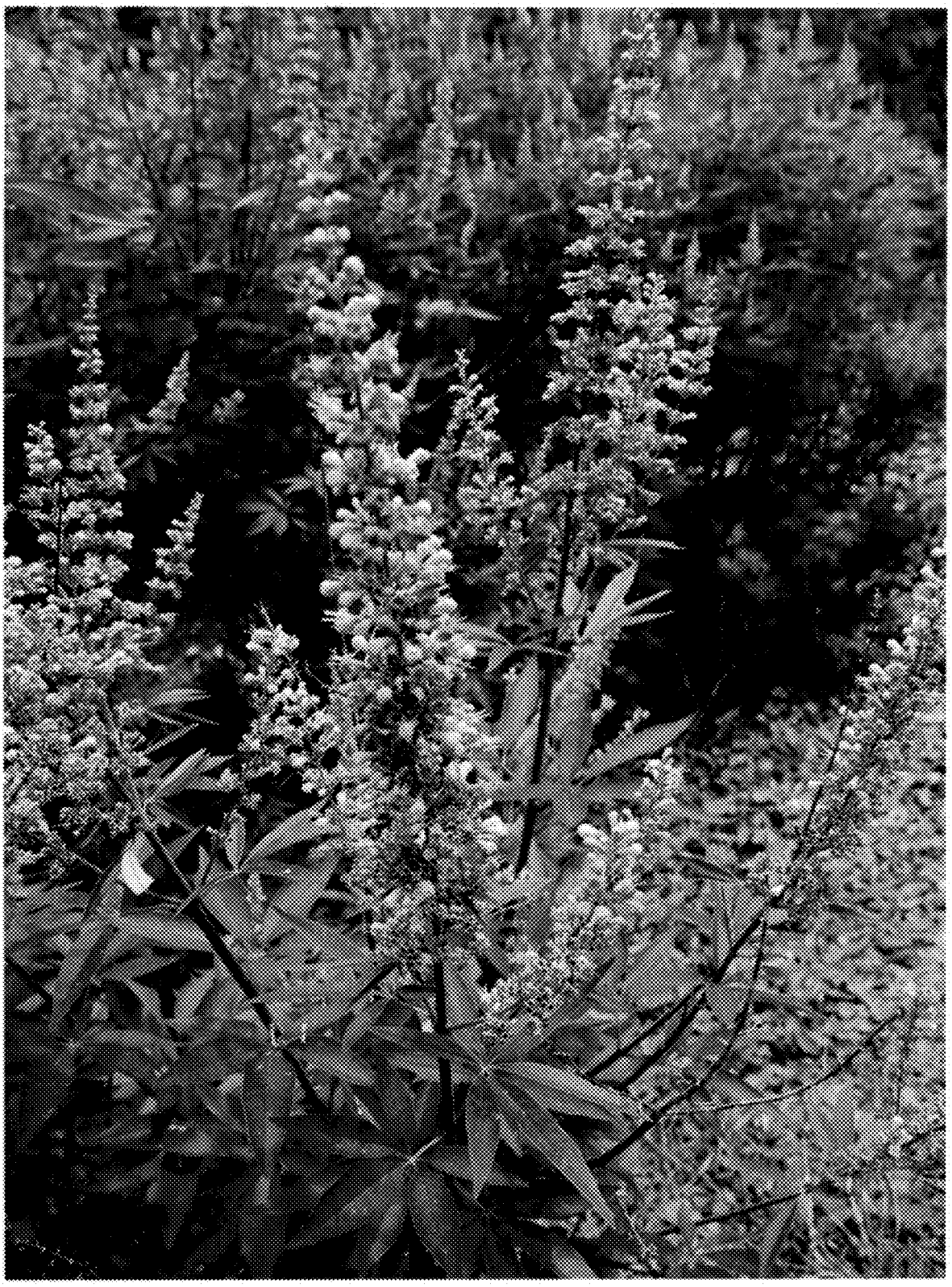
FIG. 2A shows 'Shoal Creek'.
Figure 2B:
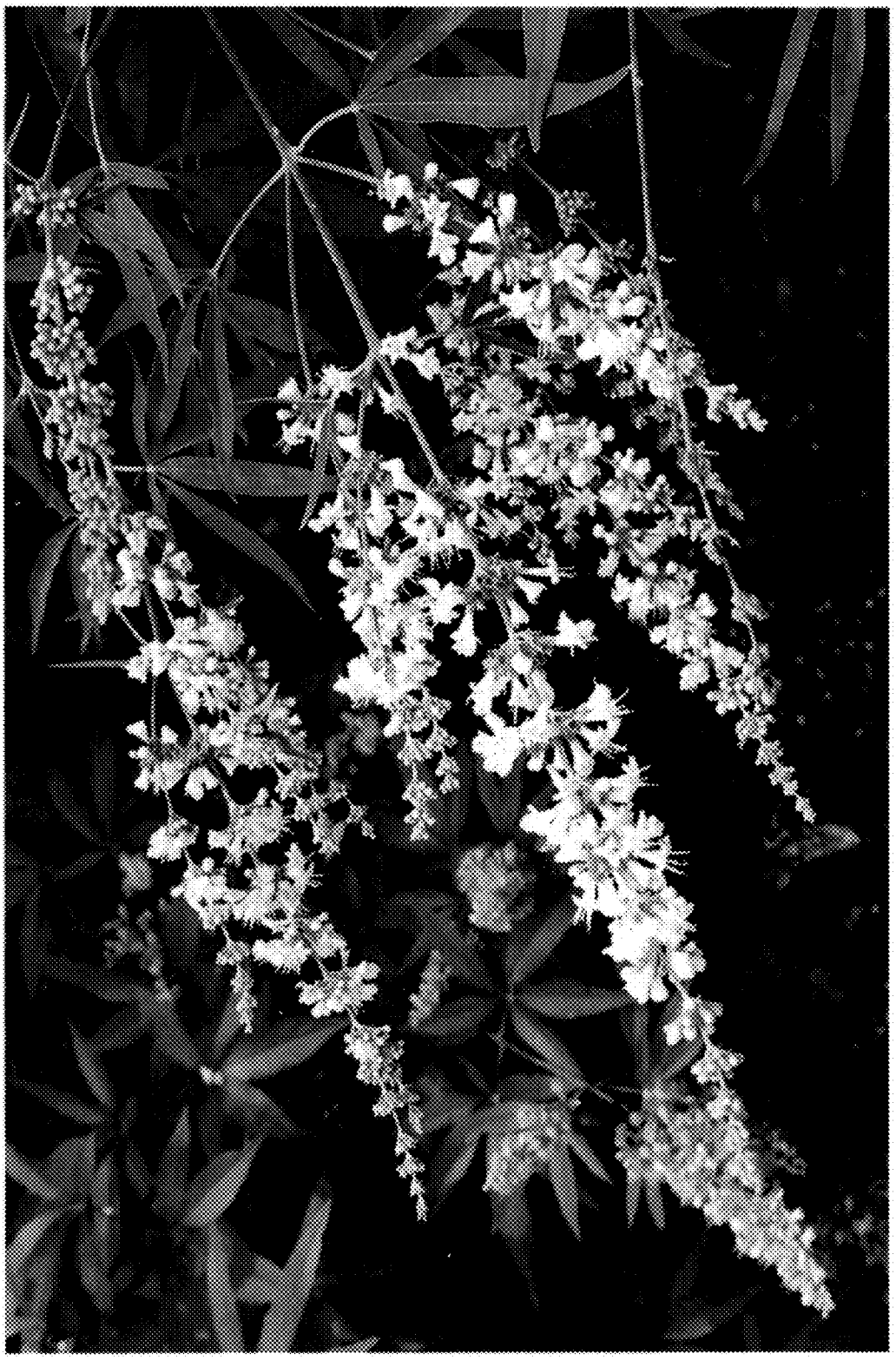
FIG. 2B shows 'Silver Spires'.
Figure 2C:
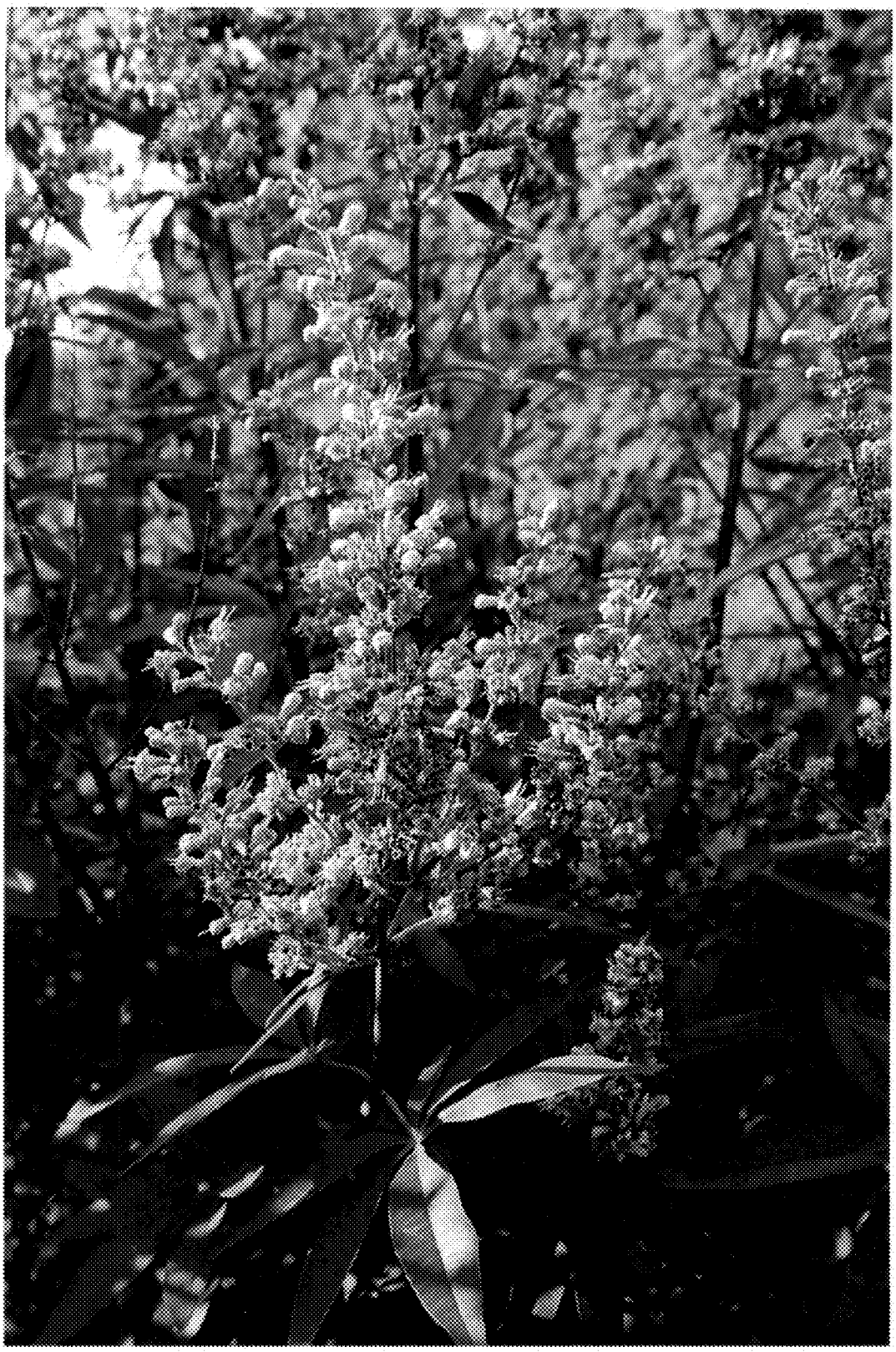
FIG. 2C shows 'Abbeville Blue'.
Figure 2D:
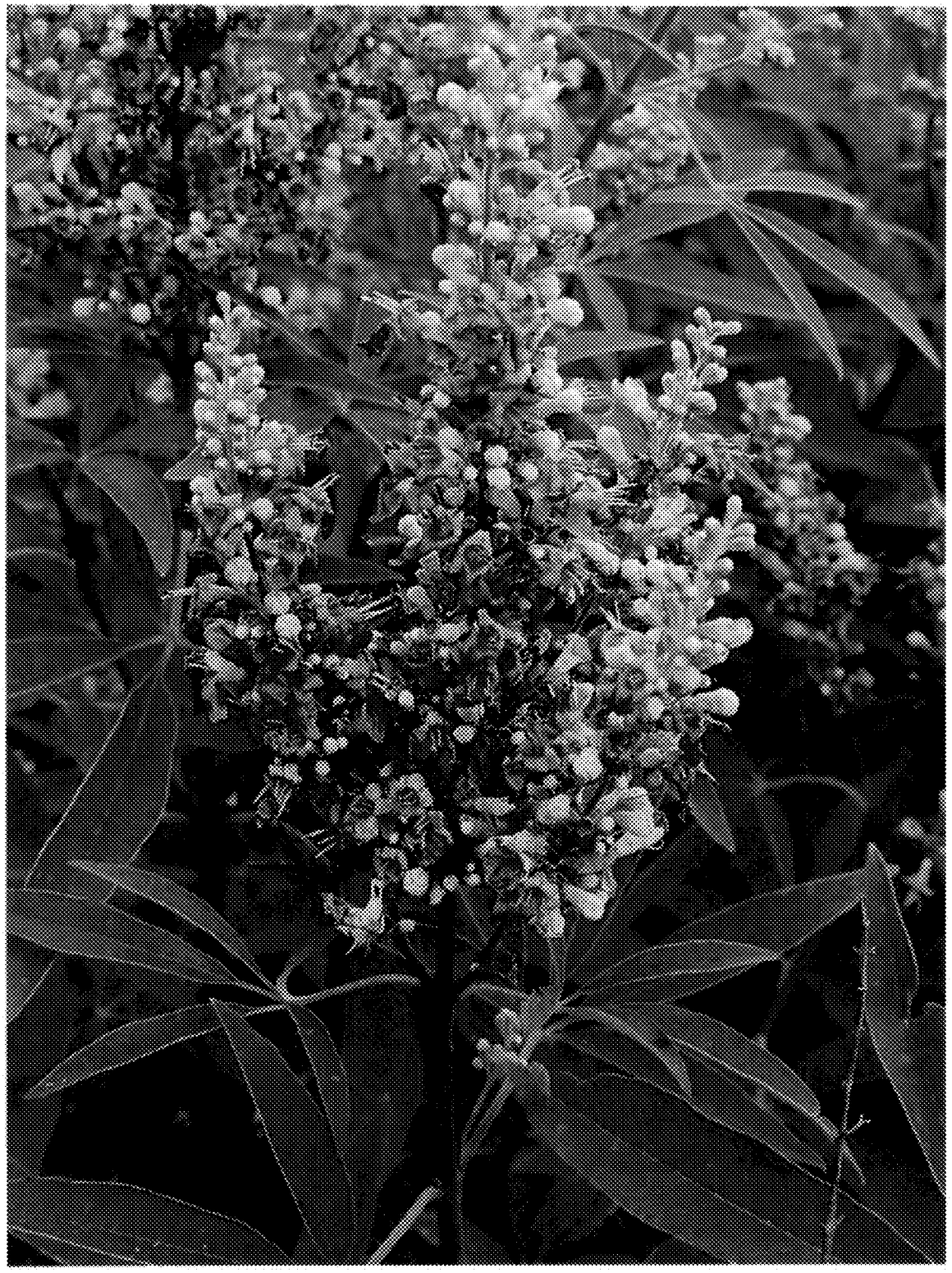
FIG. 2D shows 'V12-2-1'. 'V12-2-1' has shorter and more dense panicles. Photos were taken on Jun. 23, 2020, in a field plot in Griffin, Ga. Note the short, dense panicles of 'V12-2-1' compared to 'Shoal Creek', 'Silver Spires', and 'Abbeville Blue'.

The following traits have been consistently observed in the original plant of this new variety and in asexually propagated progeny grown from stem cuttings in Griffin and Blairsville, Georgia, and, to the best knowledge of the inventors, their combination forms the unique characteristics of the new variety 'V12-2-1'.

Throughout this specification, color names beginning with a small letter signify that the name of that color, as used in common speech, is aptly descriptive. Color names beginning with a capital letter designate values based upon The R.H.S. Colour Chart, 5$^{th}$ edition published by The Royal Horticultural Society (R.H.S.), London, England in 2007, except where general terms of ordinary dictionary significance are used.

The aforementioned photographs and following observations, measurements, and values describe plants of the *Vitex* cultivar named 'V12-2-1'. Where dimensions, sizes, colors and other characteristics are given, it is to be understood that such characteristics are approximations and averages set forth as accurately as practicable.

Data were collected from 'V12-2-1' plants propagated from softwood stem cuttings and grown in one-gallon containers prior to planting in field plots in Griffin, Georgia. Data are from 'V12-2-1' plants planted and grown in the field since 2013 and 2016. 'Abbeville Blue' and 'Shoal Creek', plants used for comparisons, were planted in 2010 and 2016 and 'Silver Spires' was planted in 2010 and 2015.

Botanical classification: *Vitex* 'V12-2-1'.

Commercial classification: Shrub or small tree.

Parentage: Initial cross between the cultivar *V. agnus-castus* 'Shoal Creek' (unpatented female parent) and either *V. agnus-castus* 'Shoal Creek' or 'Silver Spires' (unpatented male parent). A seedling from this cross, labeled V0504B-38, was planted in the field in Griffin, Ga. Seeds were collected from open pollination of V0504B-38. These seeds were germinated, and one of the resulting seedlings was selected and labeled 'V12-2-1'.

Size: 179 cm tall by 264 cm wide, measured at highest and widest point. Size is reflective of habit, i.e., 2' by 3' is rounded to broad-rounded.

Habit: Open, spreading, upright.

Stems:

*First year.*—Color: N199A. Diameter: 4-5 mm. Pubescence: covered in tiny hairs — scattered longer hairs. Exfoliation: none. Shape: Rounded. Pith: Type: Solid. Diameter: 2 mm. Color: N155D. Odor: strong, spicy, acrid. Internode Length: 4.5 cm. Strength: Strong.

*Second year.*—Color: N200A. Diameter: 6 mm. Exfoliation: none.

Vegetative buds:

*Arrangement.*—Opposite to slightly alternate.
*Type.*—Valvate.
*Size.*—1 mm×1 mm.
*Scale number.*—2.
*Scale color.*—177C.
*Position/disposition.*—45°.
*Number at node.*—1 or 2 vegetative.
*Pubescence.*—Scattered short hairs.
*Shape.*—Rounded.

Leaf scar:

*Shape.*—Cup shaped.
*Vascular bundle traces.*—3, horizontal.
*Pubescence.*—Minute hairs, mostly around perimeter.
*Position of bud.*—Just above.
*Color differentiation.*—144A.
*Size.*—1×2 mm.

Trunk or large stems:

*Color(s).*—N199A grey-brown with 156A grey-white areas.
*Size stem exfoliation begins on.*—5 cm.
*Diameter.*—2.5-5.0 cm.
*Texture.*—Smaller stems, mostly smooth, and larger stems starting to crack by 5 cm.

Leaf:

*Color through seasons.*—Emerging dates — mid April. Upper: 137C. Lower: 191A. Summer dates — mid July. Upper: 137A. Lower: 191A. Fall dates — Upper: N137B. Lower: 191B.
*Mature size.*—9 cm×10 cm.
*Apex.*—Acute.
*Base.*—Acute.
*Margin.*—Mostly entire.
*Shape.*—Palmate, 5-7 leaflets. Lobes: None. Sinuses: none.
*Vein color.*—147D.
*Pubescence.*—Upper surface has very sparse short hairs, surface somewhat glandular. Lower leaf has more hairs especially along midvein, very glandular surface.
*Arrangement on stem.*—Opposite to slightly alternate.
*Venation.*—Simple.
*Texture.*—Thickness: 0.3 mm. Degree of waxiness of surfaces: slightly waxy on upper surface, dull on lower.
*Odor when crushed.*—Spicy, acrid.

Petiole:

*Length.*—2-4 cm.
*Shape.*—Round.
*Color.*—Upper 146C, lower 145C.
*Pubescence.*—Densely covered in minute curved hairs.
*Diameter.*—1.5 mm.

Flower buds:

*Size (l×w).*—6 mm×3 mm.
*Color.*—95D.
*Shape.*—Teardrop.
*Pubescence.*—Glandular surface, tomentose.
*Time of full maturity (first visible).*—Early summer.

Flower:

*Inflorescence(s).*—Type: elongated compound panicle. Size (l×w): 9 cm×2.8 cm (longest subpanicle). Small: 65 cm×42 cm. Large: 200 cm×152 cm. Color: at emergence (date) —94C. full bloom (date) — 95C. fading (date) — 93B. Peduncle: Color: 194A. Pubescence: covered in minute hairs. Number of individual flowers per inflorescence: 400-500+. Length: 2-2.5 cm. Diameter: 1-2.5 mm. Strength: Strong. Aspect: 45° to branch.

*Petal(s).*—Number: gamopetalous with 5 lobes. Size: 10 mm×5 mm. Shape: zygomorphic, gamopetalous, bilabiate. Apex: 5 lobes rounded and slightly curled. Base: united, short tube. Margin: slightly curled. Pubescence: scattered short hairs with tuft of longer hairs at entrance to throat. Color at peak of bloom: upper surface — 95C. lower surface — 93D. Pedicels: color (R.H.S.) — 190C. pubescence — covered in minute hairs. length — 1-2 mm. Diameter: 1 mm. Aspect: 0 to 45°. Strength: moderate.

*Sepal(s)*.—Number: five fused. Size (l×w): 2 mm×1.5 mm. Shape: united, slightly lobed. Apex: slightly lobed. Base: united, short tubular. Margin: smooth. Pubescence: glandular, canescent. Texture: hoary. Color at peak of bloom: upper surface — 193A. lower surfaces — 193A.

*Male reproductive structures*.—Number: 4. Anther: size (l×w) — 1 mm×0.5 mm. color — N89A. shape — somewhat crescent, dorsifixed. texture/pubescence — slightly wrinkled. Filament: size (l×w) — 5.5 mm×0.5 mm. color — 85D. texture/pubescence — smooth but thickly tufted at base. Pollen color — N155D.

*Female reproductive structures*.—Pistil: shape — tubular, bifid. size (l×w) — 5 mm×0.5 mm. position (superior, inferior, etc.) — superior. color (R.H.S.) — 85D. pubescence — smooth but thickly tufted at base. Stigma: shape — round, bifid. color (R.H.S.) — 155C. pubescence — none. Style: length — 5 mm. shape — tubular. color (R.H.S.) — 85D. pubescence - glabrous, thickly tufted at base Ovary: shape — round. number — 1. pubescence — scattered short hairs, some glandular.

Fruit:

*Type*.—Drupe-like.

*Size* (*l*×*w*).—4 mm×3 mm.

*Color(s) during ripening*.—early (date) — 160C. mid (date) — 166B. late (date) — N186A.

*Shape*.—Globular.

*Number per infructescence*.—1.

*Pubescence*.—Few scattered hairs.

*Number of carpels*.—2.

*Persistence* (*effective period*).—Mid to late summer through fall into winter.

Seed:

*Shape*.—Globular.

*Size*.—4 mm×2 mm.

*Color*.—N186A, 200A when ripe.

*Number per locule per ovary per fruit*.—1.

*Germination capacity*.—30%.

*Pubescence*.—Scattered minute hairs.

What is claimed is:

1. A new and distinct cultivar of the *Vitex agnus-castus* plant named 'V12-2-1' substantially as illustrated and described herein.

* * * * *